United States Patent
Grendol et al.

(10) Patent No.: US 7,654,273 B2
(45) Date of Patent: Feb. 2, 2010

(54) DENTAL FLOSSER DISPENSER

(75) Inventors: Clark Lee Grendol, Sturbridge, MA (US); Allan Joseph Rieser, Sr., Charlton, MA (US)

(73) Assignee: Alsco Products LLC, Sturbridge, MA (US)

( * ) Notice: Subject to any disclaimer, the term of this patent is extended or adjusted under 35 U.S.C. 154(b) by 405 days.

(21) Appl. No.: 11/809,038

(22) Filed: May 31, 2007

(65) Prior Publication Data
US 2008/0295859 A1 Dec. 4, 2008

(51) Int. Cl.
A61C 15/00 (2006.01)
(52) U.S. Cl. ..................................... 132/324
(58) Field of Classification Search ............... 132/324, 132/323, 286; 206/368
See application file for complete search history.

(56) References Cited

U.S. PATENT DOCUMENTS

| | | | |
|---|---|---|---|
| 4,016,892 A | 4/1977 | Chodorow | |
| 4,462,136 A | 7/1984 | Nakao et al. | |
| 4,807,752 A | 2/1989 | Chodorow | |
| 5,261,430 A | 11/1993 | Mochel | |
| 5,279,314 A | 1/1994 | Poulos et al. | |
| 5,388,600 A | 2/1995 | Hart | |
| 5,411,041 A | 5/1995 | Ritter | |
| 5,573,021 A | 11/1996 | Grofcisk et al. | |
| 5,579,786 A | 12/1996 | Wolk et al. | |
| 5,732,820 A * | 3/1998 | Tsai | 206/369 |
| 5,829,458 A * | 11/1998 | Chodorow | 132/323 |
| 6,544,457 B1 | 4/2003 | Rieser | |
| 2003/0098037 A1 | 5/2003 | Dougan et al. | |
| 2007/0062554 A1 | 3/2007 | Dougan et al. | |

* cited by examiner

Primary Examiner—Robyn Doan
Assistant Examiner—Rachel R Steitz
(74) Attorney, Agent, or Firm—Louis J. Franco; Law Office of Louis J. Franco

(57) ABSTRACT

A Refillable dental flosser dispenser stores and sequentially dispenses a plurality of dental flossers each of which flossers has first and second sides and an edge extending between the first and second sides. The dispenser includes a housing having a refill end, a dispensing end and a housing side wall extending between the refill and dispensing ends. The housing side wall defines an internal storage cavity within which plural flossers are stored in a side-by-side serial arrangement. A dispensing-end wall combines with a housing side wall to define a side-emitting dispensing slot dimensioned so as to permit the edgewise withdrawal from within the storage cavity of only a single flosser at a time. Flossers within the storage cavity are positionally biased toward the dispensing wall for edgewise alignment with the dispensing slot such that, as each successive flosser is extracted from the storage cavity through the dispensing slot, each remaining flosser is incrementally advanced toward the dispensing-end wall by a distance corresponding to a single flosser width. A replaceable refill cartridge capable of containing plural flossers includes an open end through which flossers are sequentially fed into edgewise alignment with the dispensing slot.

18 Claims, 5 Drawing Sheets

DENTAL FLOSSER DISPENSER

BACKGROUND

Various corporations manufacture and market single-use dental "flossers" as an alternative to a continuous length of rolled floss from which a person removes a selected portion each time he or she flosses. Single-use flossers generally include a handle portion by which a user grips the flosser between his or her fingertips. A generally U-shaped portion depends from the handle and includes first and second space-apart fingers between which is strung a length of dental floss. Presently, flossers of the type described are sold in plastic bags or similar packaging. Each time a user requires a flosser, he must open the package, reach in and grab a flosser. Among other disadvantages, such retrieval exposes the flossers contained in the package to airborne germs and, inevitably, contact by the finger(s) of one seeking to remove a single flosser.

Accordingly, there exists a need for a conveniently refillable flosser dispenser that facilitates the sequential dispensing of flossers while protecting stored flossers from contact with dust, dirt and germs.

SUMMARY

In one illustrative embodiment, a flosser dispenser stores and sequentially dispenses a plurality of similarly configured single-use dental flossers. Each flosser has an elongated handle with head and tail ends, first and second mutually spaced apart fingers depending from the head end, first and second sides defining a flosser width, and a predetermined flosser side profile defined by an edge that extends between the first and second sides. A length of dental floss is strung for support between the first and second fingers.

The flosser dispenser includes a housing having (i) at least one side wall with an exterior surface and an interior surface defining an internal storage cavity with a predetermined cavity configuration, (ii) a refill opening through which a supply of dental flossers can be introduced into the storage cavity, and (iii) a dispensing end including a dispensing-end wall that, in combination with at least one of the at least one side walls, defines a side-emitting dispensing slot having predetermined slot-width and slot-length dimensions. In each of various versions, the dispenser includes a closure (e.g., a lid) for selectively closing the refill opening. The closure is alternatively (i) removable from and (ii) hingedly attached to the housing.

One set of embodiments further includes a refill cartridge externally dimensioned for selective insertion into the storage cavity through the refill opening of the housing. An illustrative refill cartridge has first and second ends and at least one cartridge side wall extending between the first and second ends and having an outer surface and inner surface defining an inner storage channel. The storage channel has a predetermined channel configuration and is capable of storing, and maintaining in a side-by-side serial arrangement, a plurality of the dental flossers. A first-end wall closes off the first end sufficiently to prevent the discharge through the first end of a flosser from the storage channel. The second end is sufficiently open to facilitate the issuance therethrough of flossers from within the storage channel. The refill cartridge is externally configured for disposition within the storage cavity of the housing such that the open second end of the cartridge is situated between the first end of the refill cartridge and the dispensing-end wall of the housing. That is, when properly situated within the cavity, the refill cartridge is oriented such that (i) relative to a flosser located within the channel, the closed first end of the cartridge and the dispensing-end wall of the housing are in opposite directions and, correlatively, (ii) a flosser that is incrementally displaced within the channel away from the first end of the cartridge is advanced toward the dispensing-end wall and, ultimately, into alignment with the dispensing slot to await extraction therethrough by a user. It will be appreciated that the storage channel of the refill cartridge serves to both store flossers and guide them for eventual edgewise alignment with the dispensing slot of the housing.

The flossers within the channel and the cavity are positionally biased by a biasing force toward the dispensing-end wall for edgewise alignment with the dispensing slot such that, as each successive flosser is removed from the cavity through the dispensing slot, each remaining flosser is incrementally advanced toward the dispensing-end wall by a distance corresponding to a single flosser width. In a typical embodiment situated for use, the housing and a refill cartridge inserted therein will be oriented such that the dispensing slot is beneath the closed first end of the cartridge; in this orientation, gravity may serve as the force biasing the flossers toward the dispensing slot. One will appreciate, however, that gravity need not be employed to positionally bias the stored flossers and that a mechanical biasing element such as a spring may be used to provide positional bias. The use of a biasing element, while complicating somewhat the fabrication, mechanics and use of the flosser dispenser, does provide the advantage of rendering the dispenser's orientation irrelevant.

The slot-width dimension is larger than a single flosser width and, in a typical embodiment, smaller than two flosser widths; that is, the slot-width is sized so as to permit the withdrawal of a single flosser aligned with the dispensing slot, while preventing the withdrawal of more than one flosser at a time. In a typical version, a flosser that is aligned with the dispensing slot is so aligned by virtue of contacting engagement between the dispensing-end wall and one of the first and second sides of the aligned flosser. Moreover, each of various embodiments is provided with a spacing structure that maintains at least a portion of the cartridge side wall out of contact with the dispensing-end wall such that the cartridge side wall does not obstruct the issuance of flossers from the dispensing slot. In alternative versions, at least one of the housing and the refill cartridge includes such a spacing structure. In some versions, the spacing structure is formed by one or more portions of a cartridge side wall that is not aligned with the dispensing slot extending farther away from the first end of the cartridge than a portion that stops short of obstructing the dispensing slot; the at least one farther-extending portion engages the dispensing-end wall to maintain a lesser-extending portion of the at least one cartridge side wall out of the flosser-dispensing passage. In alternative versions, a spacing structure depends from at least one of (i) the dispensing-end wall and (ii) the interior surface of a housing side wall to maintain the cartridge side wall entirely out of contact with the dispensing-end wall. Typically, though not necessarily, the second end of a refill cartridge "properly seated" within the storage cavity is in close proximity to the dispensing-end wall of the housing such that no more than one flosser within the storage cavity is at least partially outside of the refill cartridge.

Various embodiments are alternatively settable upon a horizontal surface, such as bathroom vanity top, or mountable to a vertical surface such as a wall or the inside of a medicine cabinet door. Accordingly, alternative versions include at least one of (i) a bracket by which a portion of the housing (e.g., a "back portion" opposite the portion including the dispensing slot) can be mounted to a vertical surface and (ii) a pedestal for supporting the housing in an elevated attitude relative to a horizontal surface. In either event, when gravity is relied upon to provide positional bias to the stored flossers, it is advantageous relative to a typically configured version to maintain space between the dispensing-end wall and a horizontal surface so that withdrawal of flossers through the dispensing slot is not inhibited, a point that will be more fully appreciated with examination of the detailed description and drawings. Moreover, maintaining the dispensing-end wall, and the dispensing slot, in an elevated attitude reduces the opportunities for water, such as water pooled on a vanity top, to enter the dispensing slot and contaminate stored flossers.

It is to be understood that various embodiments of a flosser dispenser within the scope and contemplation of the invention exclude a refill cartridge of the general type described above. One alternative version is a single-use system according to which a housing includes an initial plurality of dental flossers stored "directly" within the storage cavity. Once the supply of flossers provided is exhausted, the housing of a single-use system is simply discarded. Another version of a flosser dispenser excluding a refill cartridge is refillable and includes a refill opening for introducing replacement flossers directly into the storage cavity of the housing. In such a version, a predetermined cavity configuration renders the storage cavity capable of storing, and maintaining in side-by-side serial arrangement, a plurality of the dental flossers in a manner analogous to that in which the refill-cartridge storage channel of alternative versions maintains the desired flosser arrangement.

Although versions of a dispenser excluding a refill cartridge are clearly within the scope and contemplation of the invention, one will appreciate that the exclusion of a refill cartridge indicates manual, individualized introduction of flossers into the housing. One will furthermore appreciate that a refill cartridge provides a convenient and sanitary way of replenishing the supply of flossers within the storage cavity of the housing. More specifically, first-time purchase of a kit including a housing and "starter supply" of flossers is envisioned. The starter supply may be contained in a cartridge or housed directly in the storage cavity of the housing without a cartridge. Subsequently, refill cartridges that are "preloaded" with flossers "stacked" in side-by-side relationship would be commercially obtained as needed by a user for replenishment of the flosser supply. A commercially obtained refill cartridge would be sealed in some way to prevent contamination of the flossers contained therein. For instance, sealing the flossers within the storage channel of a refill cartridge would be at least one of (i) a tear-away cap that seals the second end of the refill cartridge until removed and discarded and (ii) an outer packaging fabricated from a material such as plastic, paper or cardboard, by way of non-limiting example.

To insert a refill cartridge into the housing, a user would remove the sealing material from the refill cartridge with the second end of the refill cartridge situated above the first end of the refill cartridge because, when all sealing material is removed, the second of the refill cartridge is open. With the housing oriented such that the dispensing end is above the open refill end of the housing, the refill cartridge is introduced second-end-first through the refill opening. The second end of the refill cartridge is advanced toward the dispensing end of the housing until its advancement is arrested by, for example, contact between a spacing structure and one of (i) the housing and (ii) the refill cartridge. With the refill cartridge full inserted, the refill opening is closed off by the closure and the assembly comprising the housing, the refill cartridge and the stacked flossers is placed into a predetermined dispensing attitude consistent with the particular embodiment. Because gravity will typically be relied upon to provide the previously described positional bias to the flossers, the refill orientation will most frequently be regarded as an "inverted" orientation, while a dispensing or "upright" orientation will be one in which the dispensing slot is beneath the refill end of the housing.

Representative, non-limiting embodiments are more completely described and depicted in the following detailed description and the accompanying drawings.

DETAILED DESCRIPTION

The following description of various embodiments of a flosser dispenser is illustrative in nature and is therefore not intended to limit the scope of the invention or its application of uses. Accordingly, the various implementations, aspects, versions and embodiments described in the summary and detailed description are in the nature of non-limiting examples falling within the scope of the appended claims and do not serve to define the maximum scope of the claims.

Figure 1:
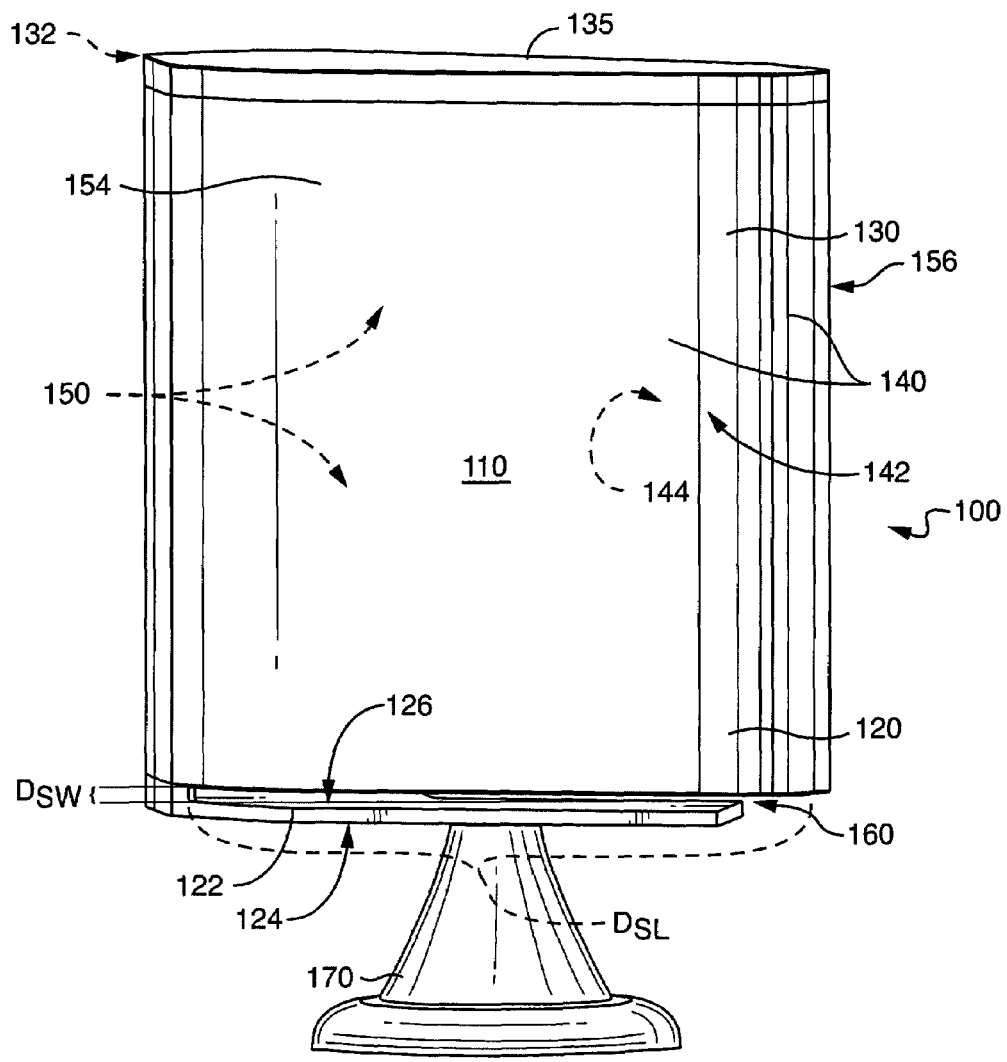
FIG. 1 is a front view of an illustrative dental flosser dispenser configured for storing and sequentially dispensing a plurality of single-use dental flossers.
Figure 1A:
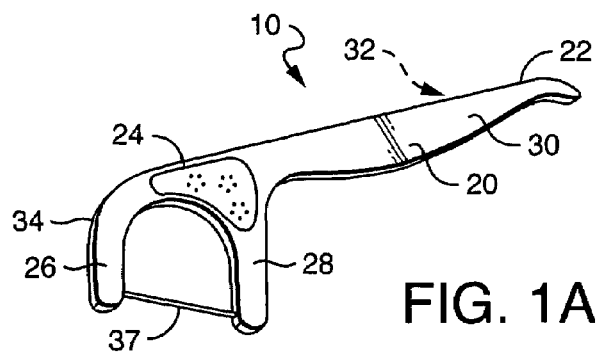
FIG. 1A shows an illustrative dental flosser of the general type the dispenser of FIG. 1 is configured to store and dispense.
Figure 2:
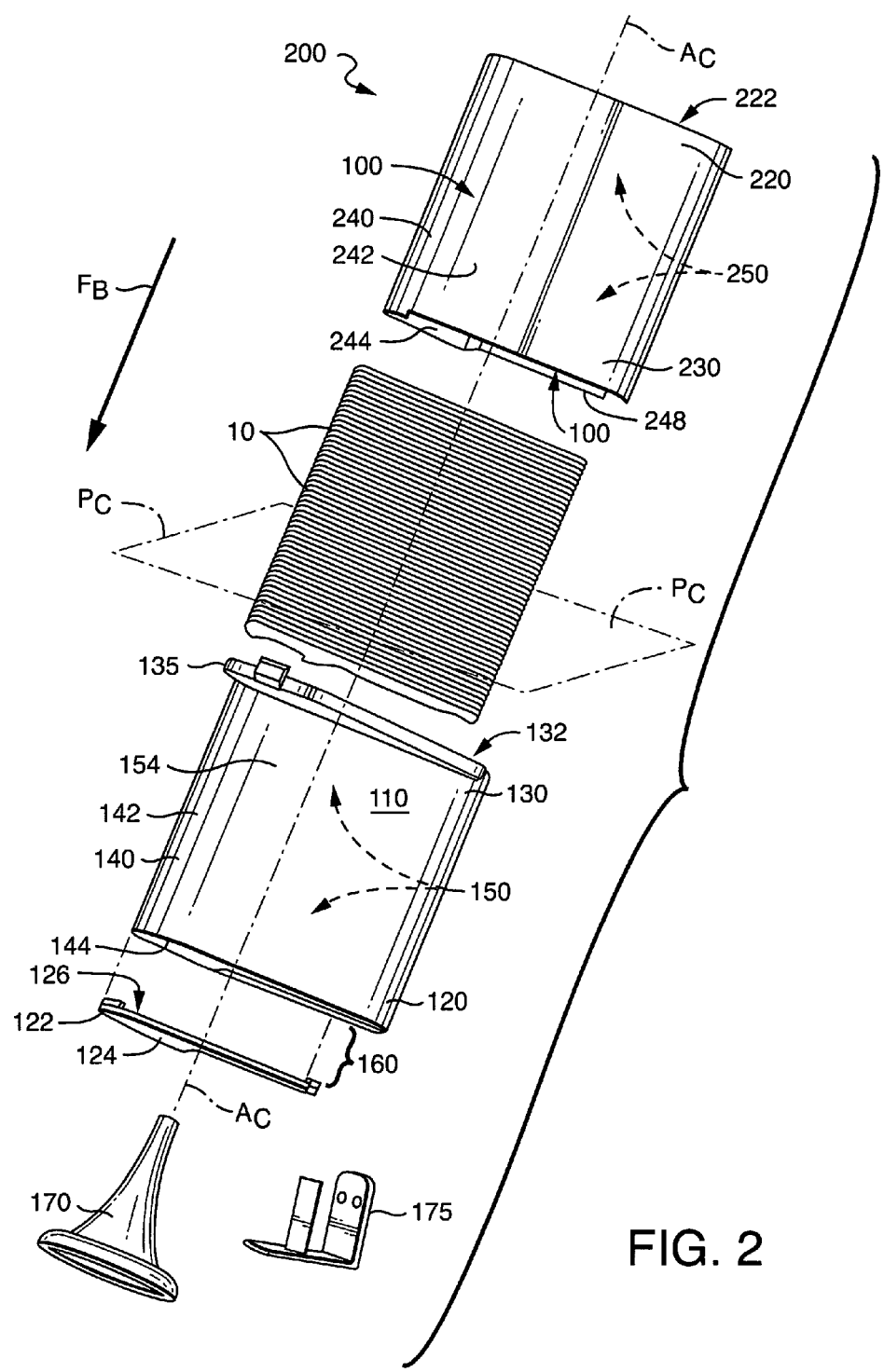
FIG. 2 is an exploded view of a dental flosser dispenser showing a housing, a refill cartridge, a plurality of "stacked" dental flossers and each of an optional pedestal and bracket.

Referring to FIGS. 1, 1A and 2, an illustrative dental flosser dispenser 100 stores and sequentially dispenses a plurality of similarly configured single-use dental flossers 10. Each flosser 10 has an elongated handle 20 with tail and head ends 22 and 24, first and second mutually spaced apart fingers 26 and 28 depending from the head end 24, first and second sides 30 and 32 defining a flosser width, and a predetermined flosser side profile defined by an edge 34 that extends between the first and second sides 30 and 32. A length of dental floss 37 is strung for support between the first and second fingers 26 and 28.

The flosser dispenser 100 includes a housing 110 having a dispensing end 120, a refill end 130 and at least one housing side wall 140 extending between the dispensing and refill ends 120 and 130 and having an exterior surface 142 and an interior surface 144 defining an internal storage cavity 150. A typical version further includes spatially opposed portions of the housing 110 regarded as front and back housing portions 154 and 156. Defined in the refill end 130 of the housing 110 is a refill opening 132 through which a supply of dental flossers 10 can be introduced into the storage cavity 150. The dispensing end 120 includes a dispensing-end wall 122 with an outside surface 124 and an inside surface 126 that, in combination with at least one of the at least one side walls 140, defines a side-emitting dispensing slot 160 having predetermined slot-width $D_{SW}$ and slot-length $D_{SL}$ dimensions. In various versions, including those depicted in the drawings, the flosser dispenser 100 includes a closure 135 (e.g., a lid) for selectively closing the refill opening 132. As shown in FIG. 2, the closure 135 may be hingedly attached to a housing side wall 140 in the vicinity of the refill end 120. Although, in the illustrative versions depicted, the refill opening 132 is indicated in a refill end 130 that is longitudinally opposite the dispensing end 120, it is to be understood that the refill opening 132, and the dispensing end 130 in which it is defined, may be alternatively located. For instance, a refill opening 132 may be defined in the front or back portion 154 or 156 of the housing. Alternatively, the dispensing-end wall 122 may open to facilitate refilling. Accordingly, nothing in the specification or drawings should be interpreted so as to limit the location of the refill opening 132 as defined in the appended claims.

As shown in FIG. 2, a typical embodiment further includes a refill cartridge 200. The refill cartridge 200 extends along a cartridge axis $A_C$ and has longitudinally opposed first and second ends 220 and 230 and at least one cartridge side wall 240 extending between the first and second ends 220 and 230. The at least one cartridge side wall 240 has an outer surface 242 and an inner surface 244 that at least partially defines an inner storage channel 250 having a predetermined channel configuration and being capable of storing, and maintaining in side-by-side serial arrangement, a plurality of similarly-configured dental flossers 10. Each flosser 10 is stored within the storage channel 250 in accordance with a predetermined storage orientation such that the first and second sides 30 and 32 of each flosser 10 extend along, though not necessary parallel to, a common plane $P_C$ that is oriented orthogonally to the cartridge axis $A_C$. A first-end wall 222 closes off the first end 220 of the refill cartridge 200 sufficiently to prevent the passage through the first end 220 of a flosser 10 from within the storage channel 250. The second end 230 has a second-end opening 232 sufficiently large to permit the passage from within the storage channel 250 of a flosser 10 oriented in accordance with the predetermined storage orientation.

The refill cartridge 200 is externally dimensioned for selective insertion into the storage cavity 150 through the refill opening 132 of the housing 110. The refill cartridge 200 is configured for disposition within the storage cavity 150 such that the second-end opening 232 of the refill cartridge 200 is situated between the first end 220 of the refill cartridge 200 and the dispensing-end wall 122 of the housing 110. That is, when properly inserted into the storage cavity 150, the refill cartridge 200 is oriented such that (i) relative to a flosser 10 located within the storage channel 250, the first-end wall 222 of the refill cartridge 200 and the dispensing-end wall 122 of the housing 110 are in opposite directions and, correlatively, (ii) a flosser 10 that is incrementally displaced within the storage channel 250 away from the first-end wall 222 is advanced toward the dispensing-end wall 122 and, ultimately, into edgewise alignment with the dispensing slot 160 to await withdrawal therethrough by a user.

When the flosser dispenser 100 is readied for use, flossers 10 within the storage channel 250 and the storage cavity 150 are positionally biased by a biasing force $F_B$ toward the dispensing-end wall 122 for alignment with the dispensing slot 160 such that, as each successive flosser 10 is extracted edgewise from the storage cavity 150 through the dispensing slot 160, each flosser 10 remaining in the storage cavity 150 is incrementally advanced toward the dispensing-end wall 122 by a distance corresponding to a single flosser width. In instances in which gravity provides the biasing force $F_B$, the housing 110 and a refill cartridge 200 inserted therein are oriented such that the first-end wall 222 of the refill cartridge 200 is above the dispending slot 160. Alternatively, a biasing element such as a spring may be included to provide positional bias and such embodiments, though not illustrated, are within the scope and contemplation of the invention as expressed in various claims appended hereto.

Figure 4:
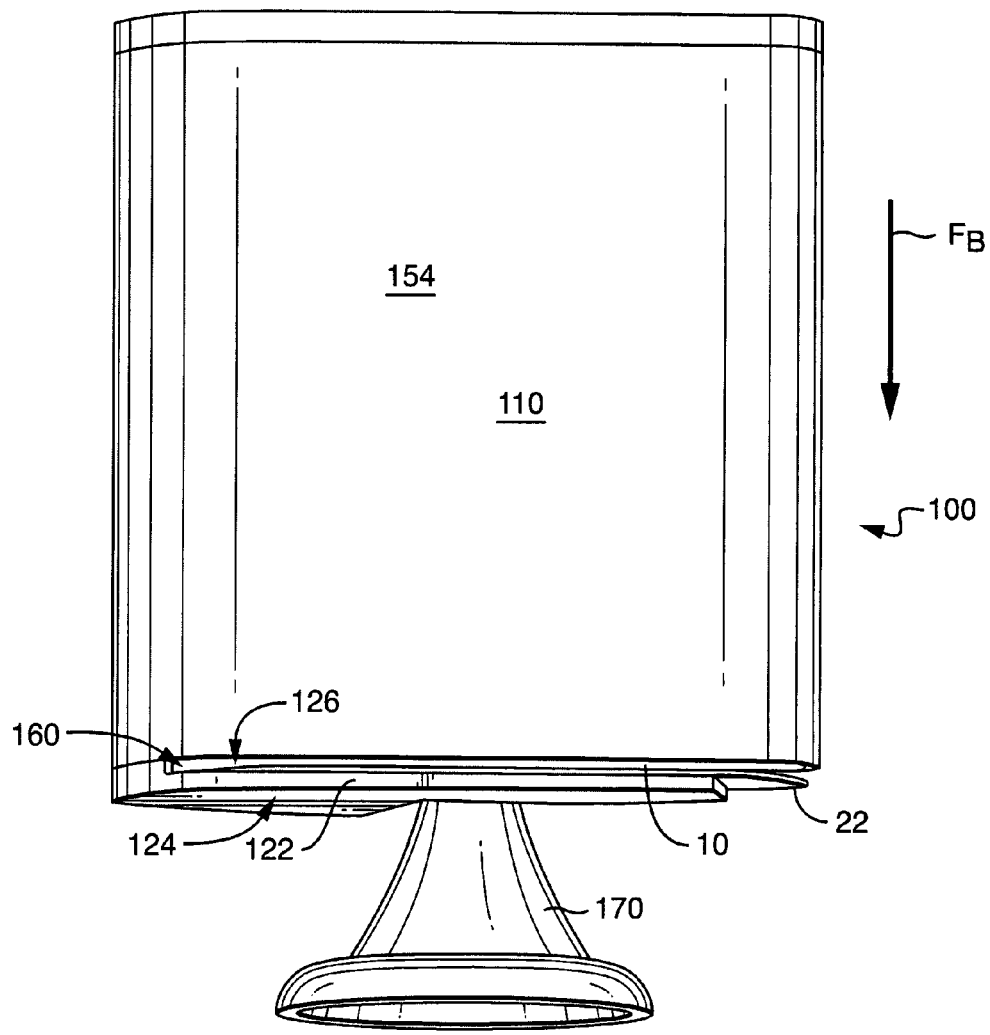
FIG. 4 is a front view of an assembled flosser dispenser with a flosser in edgewise alignment with the dispensing slot and the tail end of the flosser extending beyond the dispensing-end wall of the flosser housing in order to facilitate extraction by a user's fingers.

Referring to FIGS. 1 and 4, the slot-width dimension $D_{SW}$ is sized so as to permit the edgewise extraction from the storage cavity 250 of a single flosser 10 aligned with the dispensing slot 160, while precluding the withdrawal of more than one flosser 10 at a time. Accordingly, in a typical version, the slot width dimension $D_{SW}$ is larger than the width of a single flosser 10, but smaller than twice the width of a single flosser 10. A typical embodiment is configured such that a flosser 10 that is aligned with the dispensing slot 160 is so aligned by virtue of contacting engagement between the dispensing-end wall 122 and one of the first and second sides 30 and 32 of the aligned flosser 10. That is, the dispensing-end wall 122 defines for each successive flosser 10 a stopping position corresponding to edgewise alignment of the flosser 10 with the dispensing slot 160.

In each of various versions, at least one spacing structure ensures that no portion of a cartridge side wall 240 obstructs extraction of an aligned flosser 10 through the dispensing slot 160. In the illustrative version of FIG. 2, a spacing structure 248 is formed integrally with at least one cartridge side wall 240 and essentially comprises a portion of a cartridge side wall 240 that extends farther away from the first-end wall 222 than other portions of an at least one cartridge side wall 240. When the refill cartridge 200 is fully inserted into the housing 100, the spacing structure 248 engages the dispensing-end wall 122 such that other portions of the at least one cartridge side wall 240 do not obstruct the dispensing slot 160. Although selected drawings show one type of spacing structure 248 that depends from the refill cartridge 200, it is to be understood that within the scope and contemplation of the invention as expressed in the appended claims are versions including alternatively incorporated spacing structures. For instance, in each of various non-depicted versions, at least one spacing structure depends inwardly from the interior surface 144 of the housing side wall 140 to engage the edge of an at least one cartridge side wall 240 at the second end 230 of the refill cartridge 200.

Figure 5:
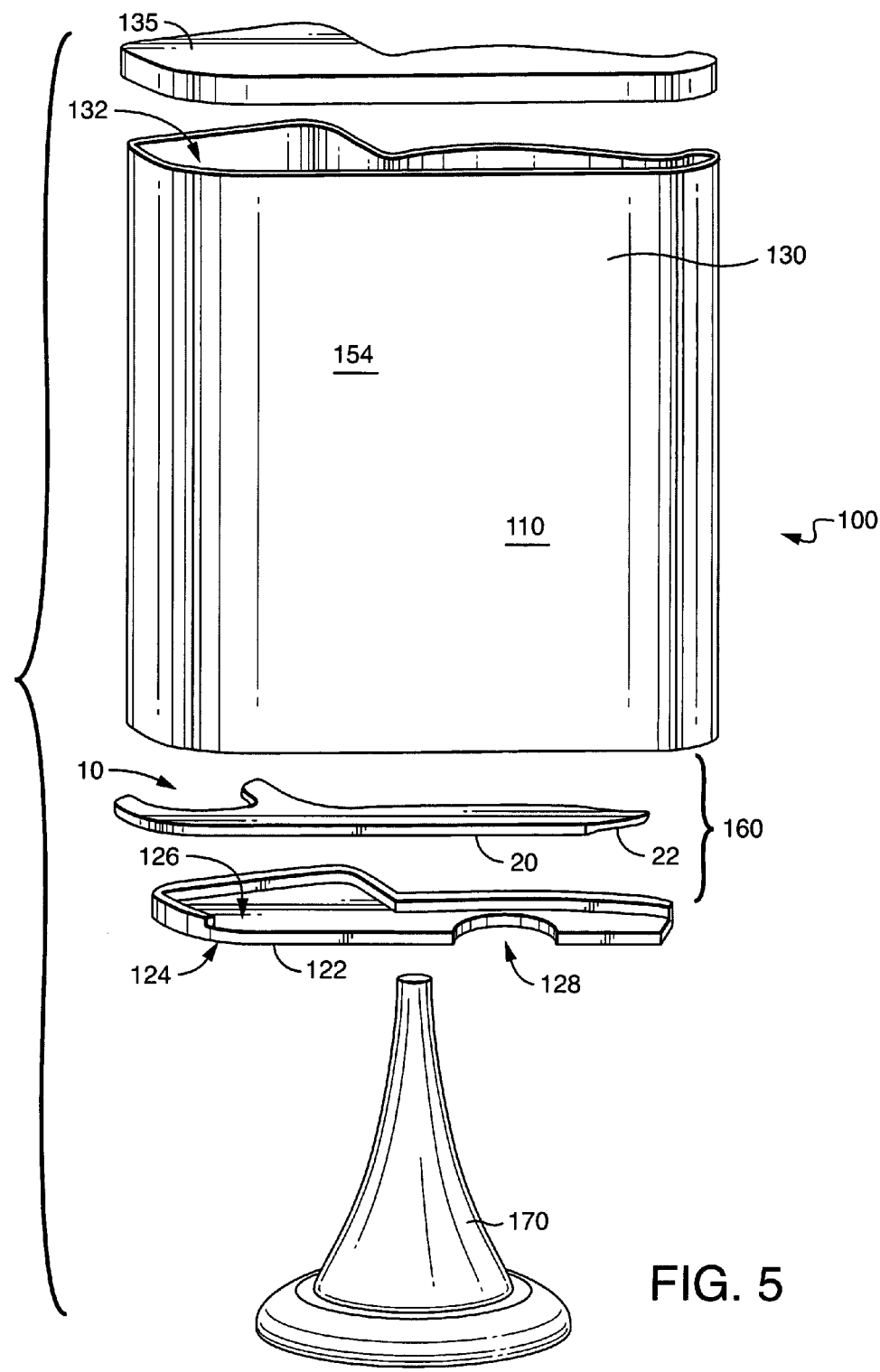
FIG. 5 is an exploded view of a flosser dispenser including a dispensing-end wall with a forward-facing notch that provides access to a flosser in edgewise alignment with the dispensing slot.

Extraction of a flosser 10 through the dispensing slot 160 is variously facilitated in alternative embodiments. For instance, with reference to the front view of FIG. 4, the dispensing-end wall 122 of the housing 110 stops short of coextension with the tail end 22 of an aligned flosser 10 such that at least a portion of the tail end 22 extends beyond the dispensing-end wall 122 for ready engagement by a user's finger (not shown). By engaging the tail end 22 of an aligned flosser 10, a user can pivot the flosser 10 such that the tail end 22 protrudes through the front housing portion 154 for grasping by a user who can then remove the flosser 10 from the housing 110 for use. Alternatively or additionally, the dispensing-end wall 122 of some versions, such as that shown in the exploded view of FIG. 5, has defined therein a notch 128 open toward the front housing portion 154. The notch 128 is typically of sufficient size to permit a user to engage with a single fingertip the handle 20 of an aligned flosser 10 and draw it forward for partial protrusion from the dispensing slot 160. With the flosser 10 partially extending through the dispensing slot 160 to the outside of the housing 110, a user can then grasp the protruding portion between two fingertips and remove the flosser 10 from the housing 110 entirely.

Figure 3:
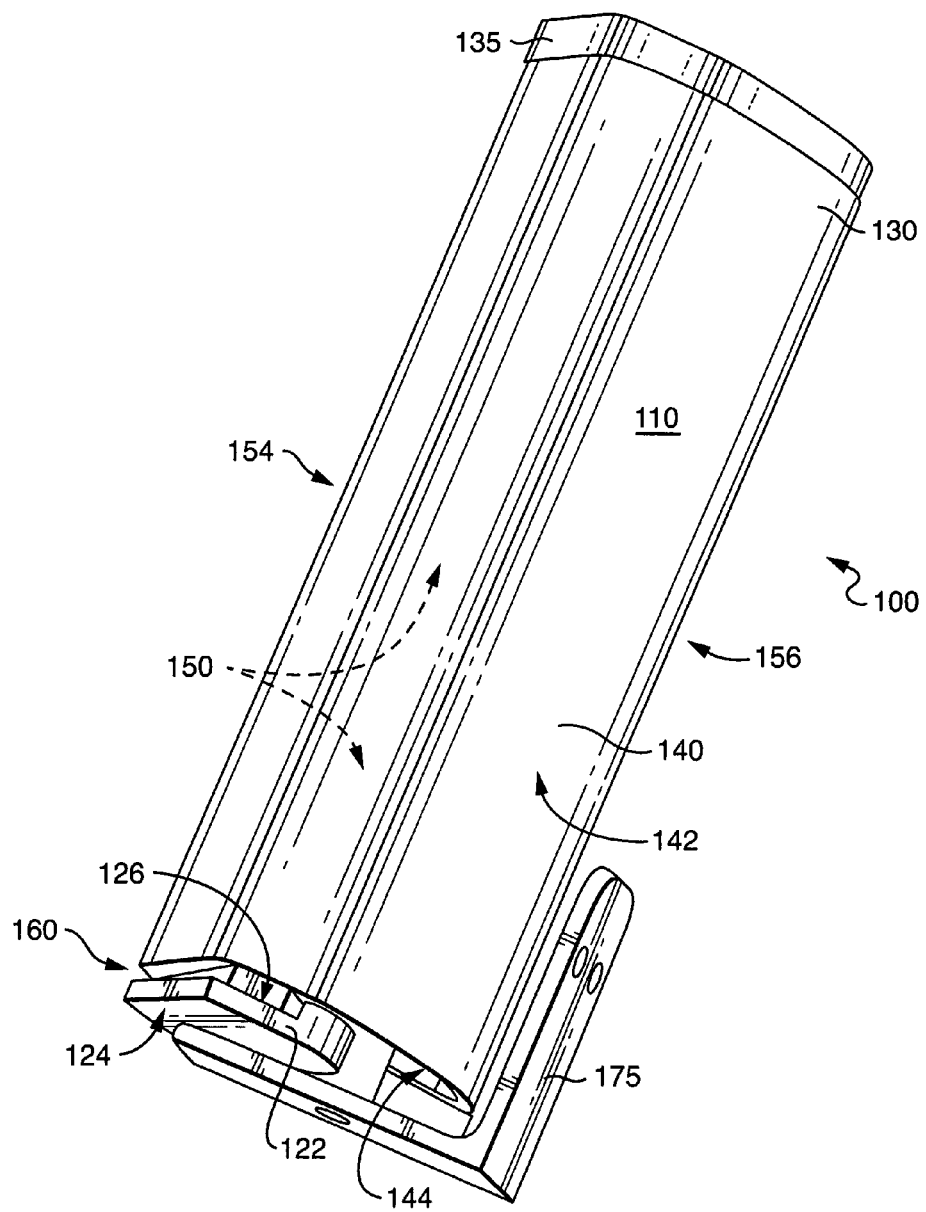
FIG. 3 is a side view of a dental flosser dispenser showing the housing engaged with a bracket configured for mounting the housing to a vertical surface.

As indicated in the summary, embodiments of a flosser dispenser 10 are alternatively mountable to a vertical surface and configured for setting upon a horizontal surface. FIGS. 1, 2, 4 and 5 variously depict embodiments including pedestals 170 that are either permanently attached or selectively engageable with the housing 110 for supporting the housing 110 on a horizontal surface (not shown). Shown in FIGS. 2 and 3 are brackets 175 by which the housing 110 of a flosser dispenser 100 can be mounted to a vertical surface such as a wall (not shown).

The foregoing is considered to be illustrative of the principles of the invention. Furthermore, since modifications and changes to various aspects and implementations will occur to those skilled in the art without departing from the scope and spirit of the invention, it is to be understood that the foregoing does not limit the invention as expressed in the appended claims to the exact constructions, implementations and versions shown and described.

What is claimed is:

1. A refillable dental flosser dispensing kit for storing and sequentially dispensing a plurality of similarly configured single-use dental flossers each of which dental flossers has an elongated handle with head and tail ends, a pair of spaced apart fingers depending from the head end and supporting a length of floss strung therebetween, first and second sides defining a flosser width, and an edge extending between the first and second sides and defining a flosser profile as viewed from one of the first and second sides, the kit comprising:

a housing having (i) at least one housing side wall with an exterior surface and an interior surface defining an internal storage cavity with a predetermined cavity configuration, (ii) a refill opening through which a supply of dental flossers can be introduced into the storage cavity, and (iii) a dispensing end including a dispensing-end wall that, in combination with at least one of the at least one housing side walls, defines a side-emitting dispensing slot having predetermined slot-width and slot-length dimensions;

a closure for selectively closing the refill opening;

a refill cartridge having at least one cartridge side wall with an outer surface defining an external cartridge configuration and an inner surface defining an inner storage channel with a predetermined channel configuration capable of storing, and maintaining in side-by-side serial arrangement in accordance with a predetermined storage orientation, a plurality of the dental flossers, the cartridge further having a first end sufficiently closed by a first-end wall to prevent the discharge from within the channel of a dental flosser and a second end that is opposite the first end and includes a second-end opening sufficiently large to facilitate the passage from within the channel of a flosser situated in accordance with the predetermined storage orientation;

wherein (i) the refill cartridge is externally configured for disposition within the storage cavity of the housing such that the second-end opening of the refill cartridge is situated between the first end of the refill cartridge and the dispensing-end wall of the housing; (ii) the slot-width dimension is sized so as to permit the edgewise extraction from the storage cavity of a single dental flosser aligned with the dispensing slot while precluding the extraction of more than one dental flosser at a time and (iii) an at least one dental flosser stored within the channel is positionally biased by a biasing force toward the dispensing-end wall for alignment with the dispensing slot such that, as each successive flosser is extracted from the storage cavity through the dispensing slot, each remaining flosser is incrementally advanced toward the dispensing-end wall by a distance corresponding to a single flosser width.

2. The kit of claim 1 wherein the closure for selectively closing the refill opening is a lid hingedly attached to at least one of the at least one housing side walls.

3. The kit of claim 1 wherein the housing and refill cartridge are configured for use in a predetermined dispensing orientation in which the dispensing slot is situated beneath the refill opening of the housing such that gravity provides the positional bias to an at least one dental flosser stored within the storage cavity.

4. The kit of claim 3 further comprising at least one of (i) a bracket by which a portion of the housing can be mounted to a vertical surface and (ii) a pedestal for supporting the housing in an elevated attitude relative to a horizontal surface.

5. The kit of claim 1 further comprising at least one of (i) a bracket by which a portion of the housing can be mounted to a vertical surface and (ii) a pedestal for supporting the housing in an elevated attitude relative to a horizontal surface.

6. A dental flosser dispenser that stores and sequentially dispenses a plurality of similarly configured single-use dental flossers each of which dental flossers has an elongated handle with head and tail ends, a pair of spaced apart fingers depending from the head end and supporting a length of floss strung therebetween, first and second sides defining a flosser width, and an edge extending between the first and second sides and defining a flosser profile as viewed from one of the first and second sides, the dispenser comprising:

a housing having (i) at least one housing side wall with an exterior surface and an interior surface defining an internal storage cavity with a predetermined cavity configuration, and (ii) a dispensing end including a dispensing-end wall that, in combination with at least one of the at least one housing side walls, defines a side-emitting dispensing slot having predetermined slot-width and slot-length dimensions;

wherein (i) the predetermined cavity configuration renders the storage cavity capable of storing, and maintaining in side-by-side serial arrangement in accordance with a predetermined storage orientation, a plurality of the dental flossers; (ii) the slot-width dimension is sized so as to permit the edgewise extraction from the storage cavity of a single dental flosser aligned with the dispensing slot while precluding the extraction of more than one dental flosser at a time and (iii) an at least one dental flosser stored within the storage cavity is positionally biased by a biasing force toward the dispensing-end wall for edgewise alignment with the dispensing slot such that, as each successive flosser is extracted edgewise from the storage cavity through the dispensing slot, each remaining flosser is incrementally advanced toward the dispensing-end wall by a distance corresponding to a single flosser width.

7. The dispenser of claim 6 further comprising at least one dental flosser stored within the storage cavity.

8. The dispenser of claim 7 further comprising (i) a refill opening through which a supply of dental flossers can be introduced into the storage cavity and (ii) a closure for selectively closing the refill opening.

9. The dispenser of claim 8 further comprising a refill cartridge having at least one cartridge side wall with an outer surface defining an external cartridge configuration and an inner surface defining an inner storage channel with a predetermined channel configuration capable of storing, and maintaining in side-by-side serial arrangement in accordance with the predetermined storage orientation, a plurality of the dental flossers, the cartridge further having a first end sufficiently closed by a first-end wall to prevent the discharge from within the channel of a dental flosser and a second end that is opposite the first end and includes a second-end opening sufficiently large to facilitate the passage from within the channel of a flosser situated in accordance with the predetermined storage orientation; wherein the refill cartridge is externally configured for disposition within the storage cavity of the housing such that the second-end opening of the refill cartridge is situated between the first end of the refill cartridge and the dispensing-end wall of the housing.

10. The dispenser of claim 9 wherein the housing and refill cartridge are configured for use in a predetermined dispensing orientation in which the dispensing slot is situated beneath the refill opening of the housing such that gravity provides the positional bias to an at least one dental flosser stored within the storage cavity.

11. The dispenser of claim 6 further comprising a refill cartridge having at least one cartridge side wall with an outer surface defining an external cartridge configuration and an inner surface defining an inner storage channel with a predetermined channel configuration capable of storing, and maintaining in side-by-side serial arrangement in accordance with the predetermined storage orientation, a plurality of the dental flossers, the cartridge further having a first end sufficiently closed by a first-end wall to prevent the discharge from within the channel of a dental flosser and a second end that is opposite the first end and includes a second-end opening sufficiently large to facilitate the passage from within the channel of a flosser situated in accordance with the predetermined storage orientation;

wherein (i) the refill cartridge is externally configured for disposition within the storage cavity of the housing such that the second-end opening of the refill cartridge is situated between the first end of the refill cartridge and the dispensing-end wall of the housing and (ii) at least one of the housing and the refill cartridge includes a spacing structure that maintains at least a portion of the cartridge side wall out of contact with the dispensing-end wall such that the cartridge side wall does not obstruct the issuance of flossers from the dispensing slot.

12. The dispenser of claim 11 wherein the housing and refill cartridge are configured for use in a predetermined dispensing orientation in which the dispensing slot is situated beneath the refill opening of the housing such that gravity provides the positional bias to an at least one dental flosser stored within the storage cavity.

13. A refillable dental flosser dispenser for storing and sequentially dispensing a plurality of similarly configured single-use dental flossers, the dispenser comprising:

a housing having (i) at least one housing side wall with an exterior surface and an interior surface defining an internal storage cavity with a predetermined cavity configuration, (ii) a refill opening through which a supply of dental flossers can be introduced into the storage cavity, and (iii) a dispensing end including a dispensing-end wall that, in combination with at least one of the at least one housing side walls, defines a side-emitting dispensing slot having predetermined slot-width and slot-length dimensions;

a refill cartridge situated within the storage cavity of the housing and having at least one cartridge side wall with an inner surface defining an inner storage channel capable of storing, and maintaining in side-by-side serial arrangement in accordance with a predetermined storage orientation, a plurality of dental flossers, the cartridge further having a first end sufficiently closed by a first-end wall to prevent the discharge from within the storage channel of a dental flosser and a second end that is opposite the first end and includes a second-end opening sufficiently large to facilitate the passage from within the storage channel of a flosser situated in accordance with the predetermined storage orientation; and a plurality of dental flossers stored within the storage channel in accordance with the predetermined storage orientation, each dental flosser having an elongated handle with head and tail ends, a pair of spaced apart fingers depending from the head end and supporting a length of floss strung therebetween, first and second sides defining a flosser width, and an edge extending between the first and second sides and defining a flosser profile as viewed from one of the first and second sides;

wherein (i) the refill cartridge is disposed within the storage cavity of the housing such that the second-end opening of the refill cartridge is situated between the first end of the refill cartridge and the dispensing-end wall of the housing; (ii) the slot-width dimension is sized so as to permit the edgewise extraction from the storage cavity of a single one of the dental flossers aligned with the dispensing slot while precluding the extraction of more than one of the dental flossers at a time and (iii) the dental flossers stored within the channel are positionally biased by a biasing force toward the dispensing-end wall for alignment with the dispensing slot such that, as each successive flosser is extracted from the storage cavity through the dispensing slot, each remaining flosser is incrementally advanced toward the dispensing-end wall by a distance corresponding to a single flosser width.

14. The dispenser of claim 13 further comprising a closure for selectively closing the refill opening of the housing.

15. The dispenser of claim 14 wherein the housing and refill cartridge are configured for use in a predetermined dispensing orientation in which the dispensing slot is situated beneath the refill opening of the housing such that gravity provides the positional bias to an at least one dental flosser stored within the storage cavity.

16. The dispenser of claim 15 further comprising at least one of (i) a bracket by which a portion of the housing can be mounted to a vertical surface and (ii) a pedestal for supporting the housing in an elevated attitude relative to a horizontal surface.

17. The dispenser of claim 13 further comprising at least one of (i) a bracket by which a portion of the housing can be mounted to a vertical surface and (ii) a pedestal for supporting the housing in an elevated attitude relative to a horizontal surface.

18. The dispenser of claim 17 wherein the housing and refill cartridge are configured for use in a predetermined dispensing orientation in which the dispensing slot is situated beneath the refill opening of the housing such that gravity provides the positional bias to an at least one dental flosser stored within the storage cavity.

* * * * *